United States Patent
Sieser et al.

(10) Patent No.: US 9,475,793 B2
(45) Date of Patent: Oct. 25, 2016

(54) CONJUGATES AND ASSOCIATED METHODS OF PRODUCING THEM FOR THE PREVENTION OR TREATMENT OF NICOTINE ADDICTION

(71) Applicant: Pfizer Inc, New York, NY (US)

(72) Inventors: Janice Ethel Sieser, Ivoryton, CT (US); Robert Alan Singer, Niantic, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 15/057,575

(22) Filed: Mar. 1, 2016

(65) Prior Publication Data

US 2016/0176846 A1    Jun. 23, 2016

Related U.S. Application Data

(62) Division of application No. 14/702,151, filed on May 1, 2015, now Pat. No. 9,303,013.

(60) Provisional application No. 61/994,627, filed on May 16, 2014.

(51) Int. Cl.
*C07D 401/04* (2006.01)
*C07C 309/30* (2006.01)

(52) U.S. Cl.
CPC .......... *C07D 401/04* (2013.01); *C07C 309/30* (2013.01)

(58) Field of Classification Search
CPC .................................................. C07D 401/04

USPC .................................................... 546/276.4
See application file for complete search history.

(56) References Cited

U.S. PATENT DOCUMENTS

| | | |
|---|---|---|
| 2005/0119480 A1 | 6/2005 | King et al. |
| 2006/0111271 A1 | 5/2006 | Cerny et al. |

FOREIGN PATENT DOCUMENTS

| | | |
|---|---|---|
| EP | A-421762 | 4/1991 |
| EP | A-1849780 | 10/2007 |
| WO | WO99/61054 | 12/1999 |
| WO | WO00/32239 | 6/2000 |
| WO | WO01/70730 | 9/2001 |
| WO | WO01/80844 | 11/2001 |
| WO | WO02/49667 | 6/2002 |
| WO | WO02/058635 | 8/2002 |
| WO | WO03/082329 | 10/2003 |
| WO | WO2005/040338 | 5/2005 |

OTHER PUBLICATIONS

Saji et al., "Synthesis and, etc.," Chem. Pharm. Bull. 45(2) 284-290 (1997).*

\* cited by examiner

*Primary Examiner* — Patricia L Morris
(74) *Attorney, Agent, or Firm* — Keith D. Hutchinson

(57) ABSTRACT

The present invention relates in part to chemical compounds, and methods for producing these compounds. The compounds may also be incorporated into compositions to enhance quit rates or reduce relapse in smoking cessation and further in treating nicotine-related dependence.

1 Claim, No Drawings

CONJUGATES AND ASSOCIATED METHODS OF PRODUCING THEM FOR THE PREVENTION OR TREATMENT OF NICOTINE ADDICTION

CROSS REFERENCE TO RELATED APPLICATIONS

This application is a Divisional Application of U.S. application Ser. No. 14/702,151, filed on May 1, 2015 (allowed), which claims the benefit of U.S. Provisional Application No. 61/994,627, filed May 16, 2014, which is incorporated herein in its entirety.

TECHNICAL FIELD

The present invention relates to processes for producing vaccine compositions containing nicotine-derived haptens, hapten-spacer conjugates and hapten-carrier conjugates that serve as the antigenic component in anti-nicotine vaccines. The invention also relates to processes for producing vaccine compositions containing such nicotine derived hapten-carrier conjugate antigens formulated with adjuvants. Such compositions are used to enhance quit rates or reduce relapse rates in smoking cessation and tobacco/nicotine dependence treatment efforts.

BACKGROUND

Smoking has many serious adverse effects on health and with many government initiatives to reduce or prevent smoking, it has become less socially acceptable. Consequently, many smokers wish to quit the habit, and while many make attempts each year, only a small minority of those who manage to quit do not relapse. The very high failure rate is the result of the addictive nature of nicotine plus the easy availability of cigarettes.

With smoking, or use of nicotine in other forms (e.g., sinus, patches, gum), nicotine enters the bloodstream and rapidly thereafter enters the brain, where it stimulates nicotinic acetylcholine receptors, causing release of dopamine, which in turn activates reward centers. With a smoking quit attempt, there is a loss of the reward response, as well as withdrawal symptoms including a decline in cognitive function. The main reason for relapse is that the loss of reward and the unpleasant withdrawal symptoms can immediately be relieved by smoking.

There are various non-vaccine therapies for smoking cessation. Nicotine replacement therapy, such as nicotine-containing chewing gum or skin patches, may help wean smokers off cigarettes but they do not break the addiction cycle that nicotine causes.

Another approach is the use of drugs that target nicotinic acetylcholine receptors, such as varenicline. Such drugs, which reduce the rewards normally encountered by smoking, have been relatively successful in aiding smoking cessation, however relapse rates are high after drug treatment ends since a lapse (e.g., smoking a single cigarette) can easily turn into a full relapse with reactivation of reward centers. More recent nicotine cessation strategies have focused on vaccines that stimulate the immune system to produce anti-nicotine antibodies that bind to nicotine in the bloodstream, thus reducing the amount and rate that nicotine can enter the brain. This in turns prevents reward centers from being activated and helps break the addiction cycle.

Since antibodies induced by vaccines can be long-living, anti-nicotine vaccines are useful both to assist in smoking cessation as well as prevention of relapse. Additionally, since the antibodies act in the periphery, there is no risk of central nervous system (eNS) adverse effects. Examples of such vaccines are described in WO00/32239, WO02/49667, WO03/82329 and US2006/111271. Nicotine derivatives are described in EP-A-421762, WO01/70730, WO01/80844 and US 2005/119480. Further nicotine derivatives have been identified under registry numbers 136400-02-7, 250683-10-4, 861023-80-5 and 861025-049. Nicotine haptens are described in WO99/61054, WO02/58635, WO03/82329, WO2005/40338 and EP-A-1849780.

SUMMARY OF THE INVENTION

In one embodiment, the invention comprises a method for producing a compound of formula (VII):

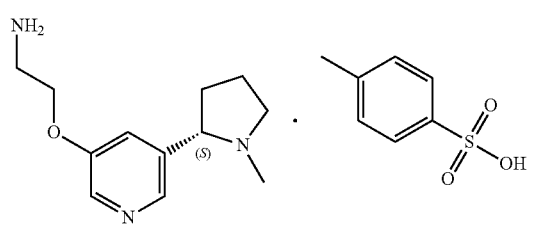

comprising the steps of: (i) combining a compound of formula (IIIA) or (IIIB):

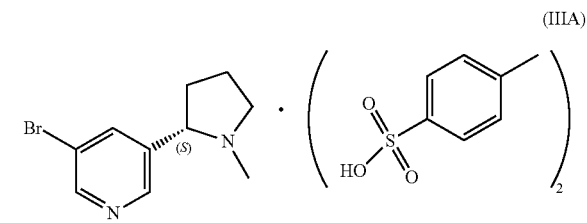

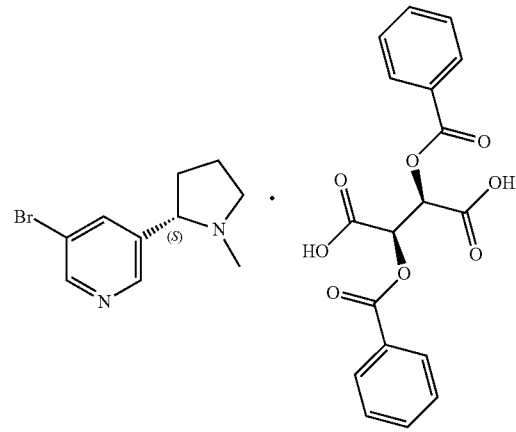

with a first base; (ii) reacting the product of step (i) with an iodide source, a metal catalyst, and a ligand; (iii) reacting the product of step (ii) with ethylene glycol, a second base and a metal catalyst; (iv) producing a compound of formula (V):

(V)

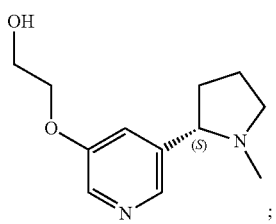

(v) reacting said compound of formula (V) with tosyl chloride and an amine base; (vi) producing and isolating a compound of formula (VI):

(VI)

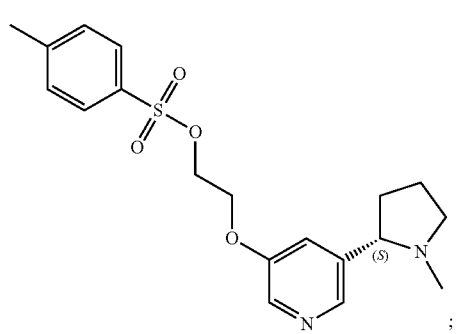

(vii) reacting said isolated compound of formula (VI) with an ammonia source; and (viii) yielding the resulting compound of formula (VII).

In another embodiment, the invention comprises a method of producing a compound of formula (VII) as herein described wherein the first base is sodium hydroxide and the second base is a carbonate base.

In a further embodiment, the invention comprises a method of producing a compound of formula (VII) as herein described wherein the metal catalyst is a copper salt.

In yet another embodiment, the invention comprises a method of producing a compound of formula (VII) as herein described wherein the ligand is a diamine.

In still another embodiment, the invention comprises a method of producing a compound of formula (VII) as herein described wherein the amine base is selected from pyridine, lutidine, 1,4-diazobicyclo[2.2.2]octane, and N-methylimidazole.

In another embodiment, the invention comprises a method of producing a compound of formula (IIIA):

(IIIA)

comprising the steps of (i) reacting a compound of formula (III):

(III)

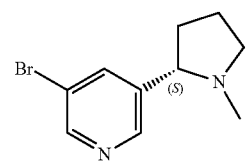

with p-toluenesulfonic acid in a solvent; and (ii) producing the compound of formula (IIIA).

In a further embodiment, the invention comprises a method of producing a compound of formula (IIIB):

(IIIB)

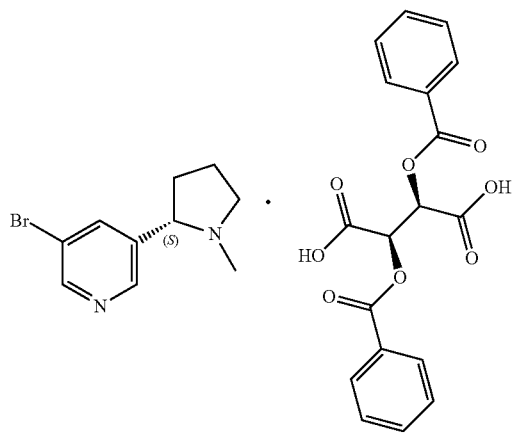

comprising the steps of: (i) reacting a compound of formula (III):

(III)

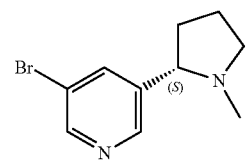

with L-DBTA in a solvent; and (ii) producing a compound of formula (IIIB).

In yet another embodiment, the invention comprises a method of producing a compound of formula (VII):

(VII)

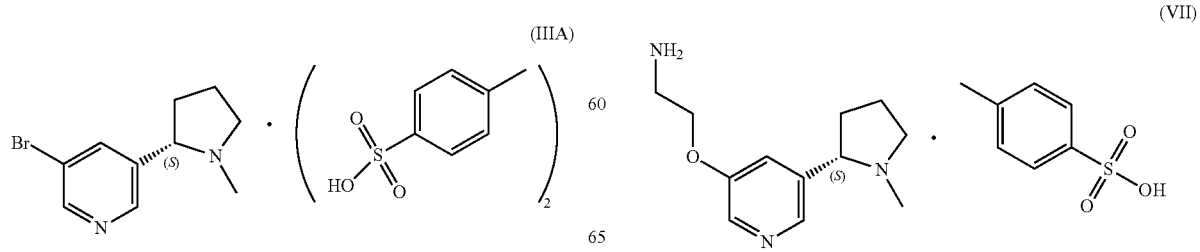

comprising the steps of: (i) reacting a compound of formula (IIIB):

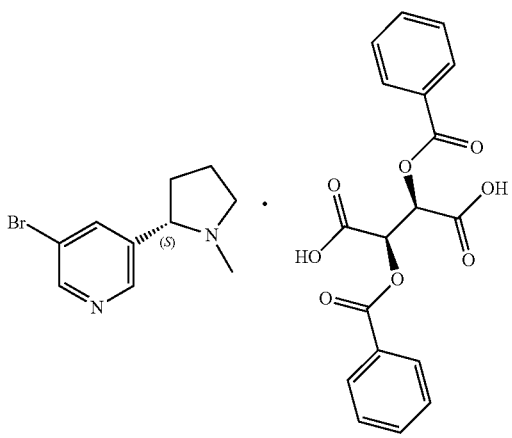

(IIIB)

with a first base; (ii) reacting the product of step (i) with an iodide source, a metal catalyst, and a ligand; (iii) reacting the product of step (ii) with ethylene glycol, a second base and a metal catalyst; (iv) producing a compound of formula (V):

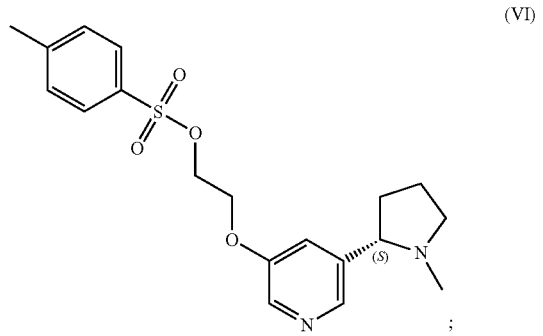

(V)

(v) reacting the compound of formula (V) with tosyl chloride and an amine base; (vi) producing and isolating a compound of formula (VI):

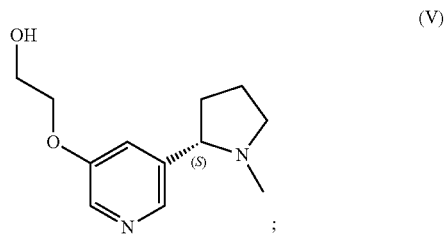

(VI)

(vii) reacting the isolated compound of formula (VI) with an ammonia source; and (viii) yielding the resulting compound of formula (VII).

In still another embodiment, the invention comprises a method of producing a compound of formula (VII) as herein described wherein the first base is sodium hydroxide and said second base is a carbonate base.

In another embodiment, the invention comprises a method of producing a compound of formula (VII) as herein described wherein the metal catalyst is a copper salt.

In a further embodiment, the invention comprises a method of producing a compound of formula (VII) as herein described wherein the ligand is a diamine.

In yet another embodiment, the invention comprises a method of producing a compound of formula (VII) as herein described wherein the amine base is selected from pyridine, lutidine, 1,4-diazobicyclo[2.2.2]octane, and N-methylimidazole.

In still another embodiment, the invention comprises a method of producing a compound of formula (VII):

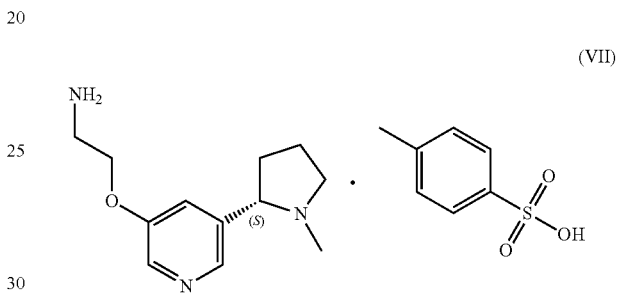

(VII)

comprising the steps of: (i) reacting a compound of formula (IIIA):

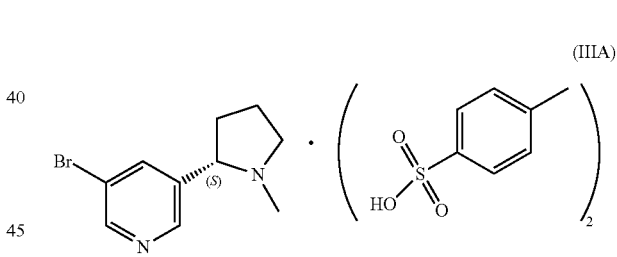

(IIIA)

with a first base; (ii) reacting the product of step (i) with an iodide source, a metal catalyst, and a ligand; (iii) reacting the product of step (ii) with ethylene glycol, a second base and a metal catalyst; (iv) producing a compound of formula (V):

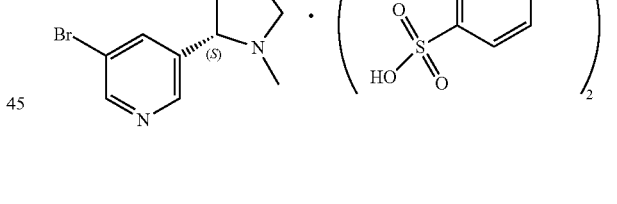

(V)

(v) reacting the compound of formula (V) with tosyl chloride and an amine base; (vi) producing and isolating a compound of formula (VI):

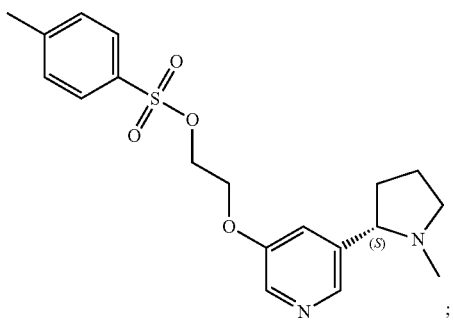
(VI)

(vii) reacting the isolated compound of formula (VI) with an ammonia source; and (viii) yielding the resulting compound of formula (VII).

In another embodiment, the invention comprises a method of producing a compound of formula (VII) as herein described wherein the first base is sodium hydroxide and said second base is a carbonate base.

In a further embodiment, the invention comprises a method of producing a compound of formula (VII) as herein described wherein the organic ligand is a diamine.

In yet another embodiment, the invention comprises a method of producing a compound of formula (VII) as herein described wherein the metal catalyst is a copper salt.

In still another embodiment, the invention comprises a method of producing a compound of formula (VII) as herein described wherein the amine base is selected from pyridine, lutidine, 1,4-diazobicyclo[2.2.2]octane, and N-methylimidazole.

In another embodiment, the invention comprises a method of producing a compound of formula (VII):

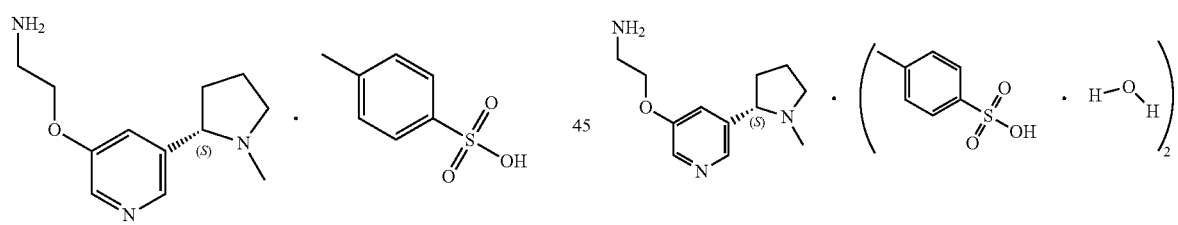
(VII)

comprising the steps of: (i) reacting a compound of formula (VI):

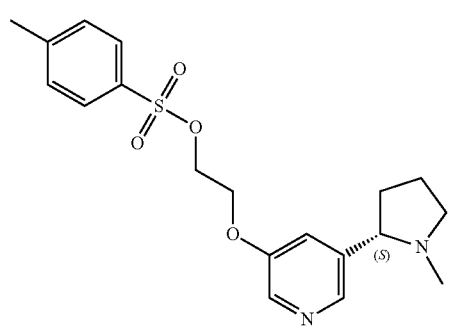
(VI)

with ammonia; and (ii) producing the resulting compound of formula (VII).

In a further embodiment, the invention comprises a compound of formula (IIIA):

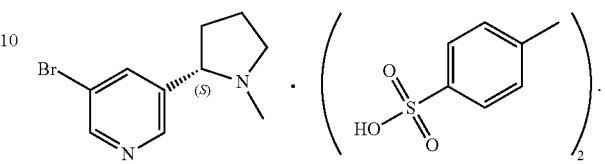
(IIIA)

In yet another embodiment, the invention comprises a compound of formula (VI):

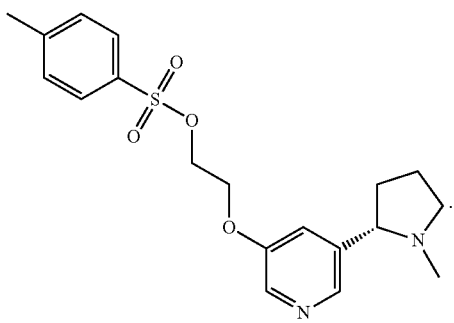
(VI)

In still another embodiment, the invention comprises a method of producing a compound of formula (VIII):

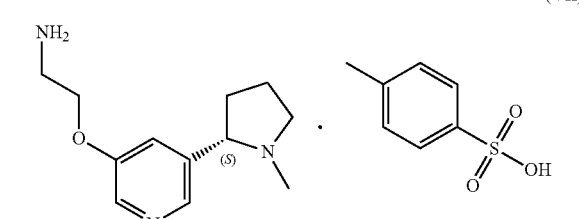
(VIII)

comprising the steps of: (i) reacting a compound of formula (VII):

(VII)

with p-toluenesulfonic acid in water and a solvent; and (ii) producing the resultant compound of formula (VIII).

DETAILED DESCRIPTION OF THE INVENTION

The present invention is illustrated by, but not limited to, the following preparations and examples, in which the following abbreviations are used.

The term "EDC" refers to 1-ethyl-3-(3-dimethylaminopropyl)carbodiimide hydrochloride.

The term "FTIR" refers to Fourier transform infrared spectroscopy.

The term "GC/MS" refers to gas chromatography-mass spectrometry.

The term "sNHS" refers to sulfo-N-hydroxysulfosuccinimide.

The term "L-DBTA" refers to L-dibenzoyltartaric acid.

$^1$H NMR (proton nuclear magnetic resonance) spectra were, in all cases, consistent with the proposed structures. Characteristic chemical shifts (δ) are given in parts-per-million downfield from tetramethylsilane using conventional abbreviations for designation of major peaks: e.g., s, singlet; d, doublet; t, triplet; q, quartet; m, multiple; br, broad; brm, broad multiplet; brt, broad triplet.

$^{13}$C NMR (carbon nuclear magnetic resonance) spectra were, in all cases, consistent with the proposed structures. Characteristic chemical shifts (δ) are given in parts-per-million, downfield (positive numbers) and upfield (negative numbers) from tetramethylsilane.

LCMS, unless otherwise indicated, was performed under the following conditions: Waters Xbridge C18 5 nm, 2.1×30 mm column, 0:100 to 95:5 gradient over 3.1 min, MeCN: (10 nM $(NH_4)_2HCO_3$ aq.).

The compounds and methods utilized herein are particularly advantageous over the prior art. One exemplary advantage is the ability to isolate one or more solid compound(s) via the disclosed methods. For example, compound VI disclosed herein may be isolated as a solid and is relatively easy to handle; the ability to purify compound VI before progressing the synthesis to the next step is particularly advantageous. Another exemplary advantage includes the elimination of dioxane or other undesirable reagents/solvents in the disclosed methods, as well as the use of safer/less hazardous reagents. A further exemplary advantage includes improved yields of desired compound(s), and more easily scalable components, conditions and processes.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers, are considered part of the invention.

Pharmaceutically acceptable salts of the compounds include the acid addition and base salts thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use*, by Stahl and Wermuth (Wiley-VCH, Weinheim, Germany, 2002).

Pharmaceutically acceptable salts of the compounds may be prepared by one or more of three exemplary methods:
(i) by reacting the compound with the desired acid or base;
(ii) by removing an acid- or base-labile protecting group from a suitable precursor of the compound or by ring-opening a suitable cyclic precursor, for example, a lactone or lactam, using the desired acid or base; or
(iii) by converting one salt of the compound to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see *J Pharm Sci*, 64 (8), 1269-1288, by Haleblian (August 1975).

Hereinafter all references to compounds include references to salts, solvates and complexes thereof and to solvates and complexes of salts thereof.

Further examples of replacement groups in accordance with the foregoing examples and examples of other prodrug types may be found in the aforementioned references.

Compounds containing one or more asymmetric carbon atoms can exist as two or more stereoisomers. Where a compound contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds containing, for example, an imino, keto, or oxime group, or so-called valence tautomerism in compounds which contain an aromatic moiety. A single compound may exhibit more than one type of isomerism.

Included within the scope of the present invention are all stereoisomers, geometric isomers and tautomeric forms of the compounds, including compounds exhibiting more than one type of isomerism, and mixtures of one or more thereof.

Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, *Stereochemistry of Organic Compounds*, by E. L. Eliel and S. H. Wilen (Wiley, New York, 1994).

The present invention includes all pharmaceutically acceptable isotopically-labelled compounds wherein one or more atoms are replaced by atoms having the same atomic number, but an atomic mass or mass number different from the atomic mass or mass number which predominates in nature.

Examples of isotopes suitable for inclusion in the compounds of the invention include isotopes of: hydrogen, such as $^2$H and $^3$H; carbon, such as $^{11}$C, $^{13}$C and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O and $^{18}$O; phosphorus, such as $^{32}$P; and sulphur, such as $^{35}$S.

Certain isotopically-labelled compounds, for example, those incorporating a radioactive isotope, are useful in drug and/or substrate tissue distribution studies. The radioactive isotopes tritium (i.e., $^3$H), and carbon-14 (i.e., $^{14}$O) are particularly useful for this purpose in view of their ease of incorporation and ready means of detection.

Substitution with heavier isotopes such as deuterium (i.e., $^2$H) may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Scheme 1: Stereoselective Synthesis of (S)-2-(5-(1-methylpyrrolidin-2-yl)pyridin-3-yloxy)ethanamine-4-methylbenzenesulfonate (VII).

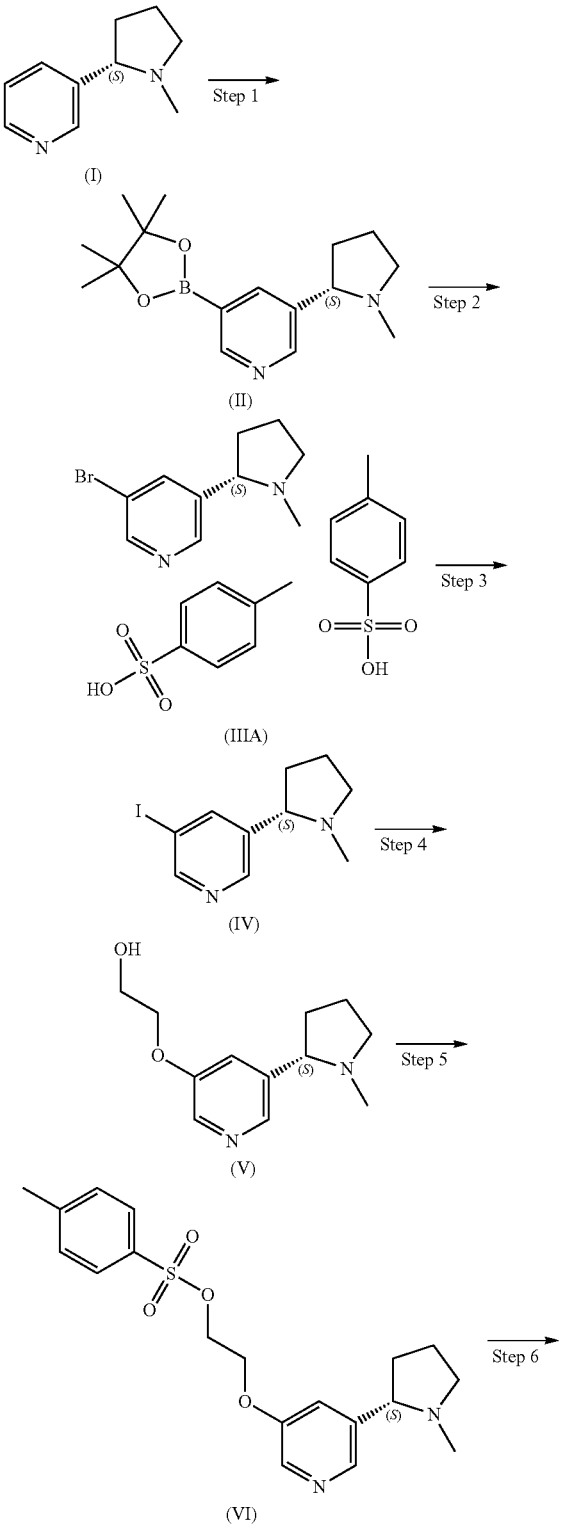

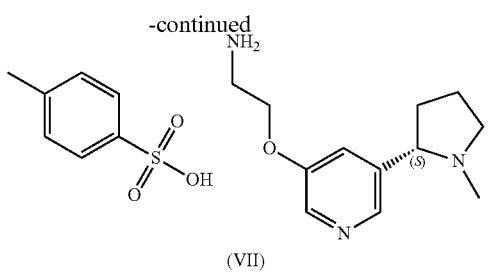

(VII)

Boronate ester (II) was formed from the reaction of (S)-(−)-nicotine (I) with a suitable iridium catalyst, typically chloro(1,5-cyclooctadiene)iridium(I) dimer, a ligand, such as 4,4'-di-tert-butyl-2,2'-dipyridyl, 3,4,7,8-tetramethyl-1,10-phenanthroline or 1,10-phenanthroline, a boron source, such as bis(pinacolato)diboron or 4,4,5,5-tetramethyl-1,3,2-dioxaborolane, in a suitable solvent, such as THF or heptane, at a temperature typically between 60° C. and reflux. Boronate ester (II) was then converted to bromide (III) using copper (II) bromide in a suitable solvent system, such as methanol or methanol/water, at a temperature between 20° C. and reflux. The bromide (III) was isolated as a crystalline salt such as the bis-tosylate (IIIA) or the L-dibenzoyl tartrate (IIIB) under standard reaction conditions with acids such as p-toluenesulfonic acid or (−)-dibenzoyl-L-tartaric acid in suitable solvents such as acetone or ethanol.

The bromide (III) was converted to iodide (IV) with sodium iodide and a suitable copper catalyst, typically cuprous iodide, in the presence of a ligand such as N,N'-dimethylethylenediamine, in a suitable solvent such as methyl isobutyl ketone, 1-butanol or 1,4-dioxane, at a temperature around 100° C.

The iodide (IV) reacted with ethylene glycol and a suitable copper catalyst, typically cuprous iodide, in the presence of a suitable base, typically potassium carbonate, at a temperature around 100° C., to form the alcohol (V).

Esterification of the alcohol (V) to the sulfonate (VI) was carried out under standard reaction conditions with p-toluenesulfonyl chloride and a suitable base such as pyridine or N-methylimidazole, in a suitable solvent such as toluene or dichloromethane, at a temperature between −10 and 20° C. The sulfonate (VI) was then recrystallized from a suitable solvent system such as ethyl acetate/heptane or tert-butyl methyl ether/heptane.

Conversion of the sulfonate (VI) to the amine was accomplished by reacting the sulfonate (VI) with ammonia, in a suitable solvent, typically methanol, in a closed system, at a temperature typically between 65 and 100° C. The tosylate salt (VII) was then isolated from the reaction by addition of a suitable solvent, typically acetonitrile, after distillation of the ammonia and reaction solvent.

Scheme 2: Preparations of S)-3-bromo-5-(1-methylpyrrolidin-2-yl)pyridine-bis (4-methylbenzenesulfonate) (IIIA) and S)-3-bromo-5-(1-methylpyrrolidin-2-yl)pyridine (2R,3R)-2,3-bis (benzoyloxy) succinate (IIIB).

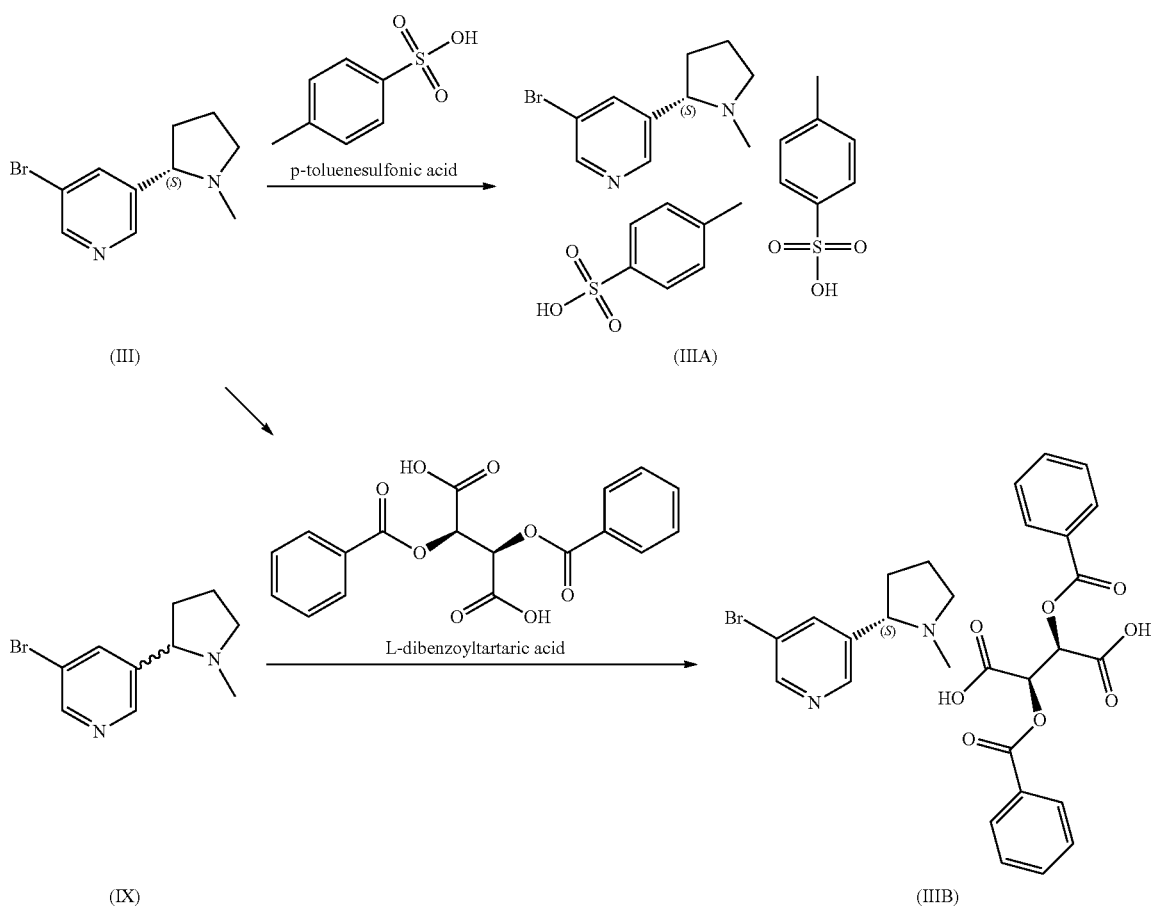

Scheme 3: Preparation of (S)-2-((5-(1-methylpyrrolidin-2-yl)pyridin-3-yl)oxy)ethan-1-amine bis(4-methylbenzenesulfonate) dihydrate (VIII).

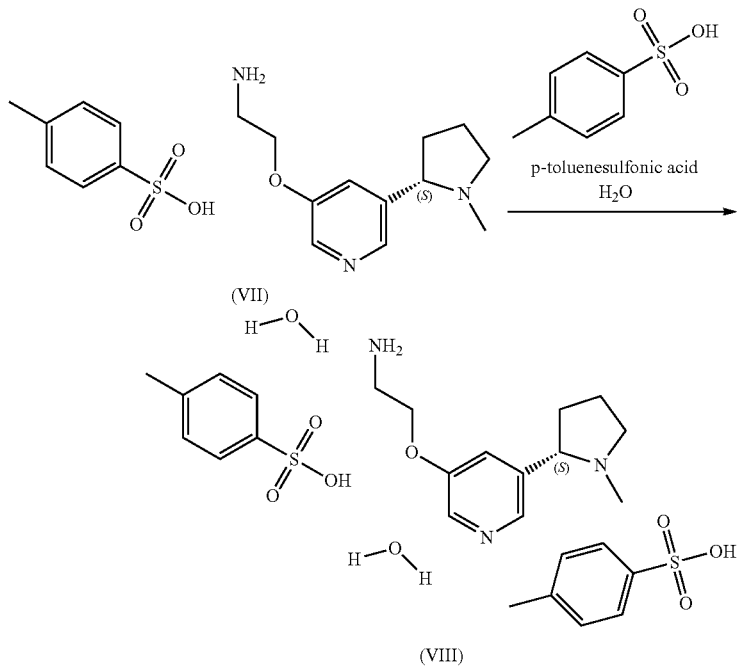

Preparations

Preparation 1: (S)-3-(1-methylpyrrolidin-2-yl)-5-(4,4,5,5-tetramethyl-1,3,2-dioxaborolan-2-yl)pyridine (II)

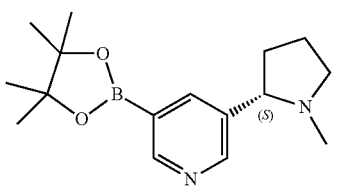

Anhydrous Heptane (10 mL) was charged to a reaction vessel equipped with FTIR probe, reflux condenser and N₂ sparge tube. N₂ was bubbled into the heptane for 30 minutes. The N₂ sparge tube was removed and substituted with a N₂ sweep of headspace. Bis(Pinacolato)diboron (1.1740 g, 4.62 mmol, 0.75 equiv.), Nicotine (I) (1.00 g, 6.16 mmol, 1.00 equiv.)), 3,4,7,8-tetramethyl-1,10-phenanthroline (0.0297 g, 0.123 mmol, 0.020 equiv.) and chloro(1,5-cyclooctadiene)iridium(I) dimer (0.0418 g, 0.0616 mmol, 0.010 equiv.) were added to the reaction vessel.

The suspension was heated to a target temperature of 90° C. At 45° C., all solids dissolved into an orange solution. The reaction looked nearly complete by FTIR trend data by the time the reaction reached the target temperature of 90° C. GC/MS analysis indicated approximately 99% conversion to product from nicotine after 75 minutes at target temperature.

The reaction was cooled to 20° C. and filtered to isolate a yellow solid (1.707 g). Potency of the solid was determined by QNMR to be 80% giving a corrected isolated yield of 1.366 g, 77% (S)-3-(1-methylpyrrolidin-2-yl)-5-(4,4,5,5-tetramethyl-1,3,2-dioxaborolan-2-yl)pyridine (II).

Preparation 2: (S)-3-bromo-5-(1-methylpyrrolidin-2-yl)pyridine (2R,3R)-2,3-bis(benzoyloxy) succinate (IIIB)

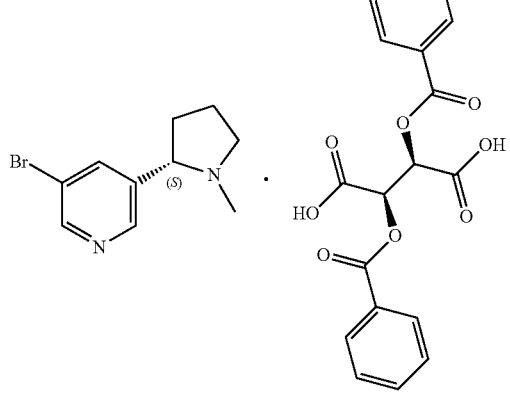

(S)-3-(1-methylpyrrolidin-2-yl)-5-(4,4,5,5-tetramethyl-1,3,2-dioxaborolan-2-yl)pyridine (II) (1.69 g, 5.88 mmol, 1.0 equiv.) was dissolved in methanol (22 mL) by heating to 45-50° C. A solution of cupric bromide (3.49 g, 15.6 mmol, 2.6 equiv) in water (22 mL) was slowly added to the amber methanol solution forming a thick green suspension. GC/MS analysis indicated reaction completion after 1 hour at 50° C.

Isopropyl acetate (22 mL) and ammonium hydroxide (28 mass %, 13.5 mL) were added to the mixture after cooling to 20° C. The phases were split and the aqueous layer extracted again with isopropyl acetate (11 mL). The combined organic layers were washed with ammonium hydroxide (28 mass %, 7 mL) diluted in water (22 mL) followed by saturated aqueous NaCl (13.5 ml) then dried over $Na_2SO_4$. The dried isopropyl acetate solution of (S)-3-bromo-5-(1-methylpyrrolidin-2-yl)pyridine (III) was filtered and concentrated to an amber oil to be carried forward for isolation as desired salt.

A solution of (−)-dibenzoyl-L-tartaric acid monohydrate (2.11 g, 5.89 mmol, 1.0 equiv) in ethanol (22 mL) was added to (S)-3-bromo-5-(1-methylpyrrolidin-2-yl)pyridine (III) (5.88 mmol, 1.0 equiv) dissolved in ethanol (22 mL) at 20° C. Solids precipitated and the mixture was granulated 18 hours. The light yellow solids filtered from the mixture were washed with ethanol and dried on the filter, giving (S)-3-bromo-5-(1-methylpyrrolidin-2-yl)pyridine (2R,3R)-2,3-bis (benzoyloxy) succinate (IIIB) (2.9556 g, 84%, 99.5% ee).

$^1$H NMR (400 MHz, methanol-$d_4$) δ 2.05-2.19 (m, 3H) 2.35-2.50 (m, 1H) 2.58-2.63 (m, 3H) 3.02-3.16 (m, 1H) 3.65-3.75 (m, 1H) 4.16-4.25 (m, 1H) 5.89 (s, 2H) 7.41-7.49 (m, 5H) 7.58 (tt, 2H) 8.06-8.09 (m, 2H) 8.09-8.12 (m, 2H) 8.24 (t, 1H) 8.59 (d, 1H) 8.69 (d, 1H) 8.69 (d, 1H).

$^{13}$C NMR (400 MHz, methanol-$d_4$) δ 13.91, 20.96, 31.01, 37.64, 55.73, 73.22, 128.10, 129.51, 129.56, 133.04, 138.93, 147.93, 151.19, 165.56, 169.74.

Preparation 3: (S)-3-bromo-5-(1-methylpyrrolidin-2-yl)pyridine-bis (4-methylbenzenesulfonate) (IIIA)

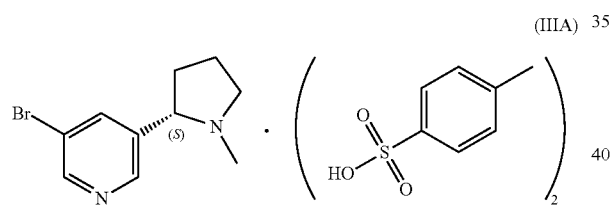

Bis(pinacolato)diboron (4.70 kg, 18.49 mol, 0.75 equiv.), 4,4'-di-tert-butyl-2,2'-dipyridyl (0.41 kg, 1.48 mol, 0.06 equiv), and (S)-Nicotine (I) (4.00 kg, 24.66 mol, 1.00 equiv) were added to anhydrous tetrahydrofuran (40.00 L) in a nitrogen purged reactor. Nitrogen was bubbled vigorously into the colorless solution for 30 minutes before and after charging chloro (1,5-cyclooctadiene) iridium(I) dimer (0.50 kg, 0.74 mol, 0.03 equiv.). A nitrogen sweep of the headspace was maintained as the mixture was heated and held at 60° C. for 18 hours. GC/MS analysis indicated >95% conversion to the borinate ester (II) from Nicotine (I). The solution was concentrated under vacuum. Tetrahydrofuran was replaced with methanol giving an orange suspension of (S)-3-(1-methylpyrrolidin-2-yl)-5-(4,4,5,5-tetramethyl-1,3,2-dioxaborolan-2-yl)pyridine (II) in methanol (36 L).

A solution of cupric bromide (16.52 kg, mol, equiv.) in water (30 L) was added over 30 minute at 20° C. to the methanol suspension. GC/MS analysis indicated reaction completion after 12 hours at 20° C. Isopropyl acetate (40.00 L) and ammonium hydroxide (28 mass %, 24.00 L) were added to the mixture with stirring. The phases were split and the aqueous layer extracted again with isopropyl acetate (20.00 L). The combined organic layers were washed with ammonium hydroxide (28 mass %, 2.80 L) diluted in water (5.60 L) followed by a solution of sodium chloride (2.15 kg) in water (15.04 L). The isopropyl acetate solution of (S)-3-bromo-5-(1-methylpyrrolidin-2-yl)pyridine (III) was concentrated to an amber oil to (~12 L) be carried forward for isolation as desired salt.

The crude oil containing (S)-3-bromo-5-(1-methylpyrrolidin-2-yl)pyridine (III) was dissolved in acetone (4.0 L). An acetone (16.0 L) solution of p-toluenesulfonic acid (9.38 kg, 49.3 mol, 2.0 equivalents) was added over 30 min at 15° C. The hazy mixture was seeded with (S)-3-bromo-5-(1-methylpyrrolidin-2-yl)pyridine bis (4-methylbenzene-sulfonate) (IIIA) (30 g, 0.051 mol, 0.002 equivalents) and cooled to 0° C. After 2 hours at 0° C., the mixture was filtered and the white solids washed with cold acetone. (S)-3-bromo-5-(1-methylpyrrolidin-2-yl)pyridine bis (4-methylbenzenesulfonate) (IIIA) (9.69 kg, 16.52 mol, 67%, corrected yield) was isolated after drying on the filter for 16 hours.

$^1$H NMR (400 MHz, DMSO-$d_6$) δ 2.13 (m, 2H), 2.23 (m, 1H), 2.29 (s, 3H), 2.45 (m, 1H), 2.72 (d, 3H), 3.24 (m, 1H), 3.78 (m, 1H), 4.49 (q, 1H), 7.14 (d, 2H), 7.50 (d, 2H), 8.33 (t, 1H), 88.73 (d, 1H), 8.83 (d, 1H).

$^{13}$C NMR (400 MHz, DMSO-$d_6$) δ 20.8, 21.3, 30.5, 38.2, 55.6, 68.1, 120.5, 125.5, 128.2, 131.1, 137.9, 139.0, 145.2, 148.7, 151.5.

Preparation 4: (S)-3-iodo-5-(1-methylpyrrolidin-2-yl)pyridine (IV)

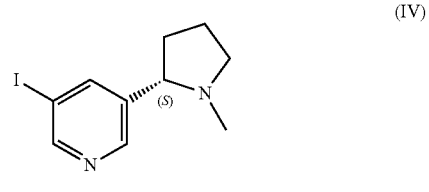

(S)-3-bromo-5-(1-methylpyrrolidin-2-yl)pyridine bis (4-methylbenzenesulfonate) (IIIA) (23.4 k g, 39.96 mol, 1.00 equivalent) was dissolved in water (117 L). Methyl isobutyl ketone (117 L) was added to the solution forming two phases.

An aqueous solution of sodium hydroxide (18.9 mol/L, 4.24 L, 79.92 mol, 2.0 equiv.) was added to the mixture resulting in a change in pH of the aqueous layer from 2 to 12. The phases were split after stirring 15-20 minutes. The lower yellow aqueous layer was extracted again with methyl Isobutyl ketone (23.4 L) and then discarded. The combined organic extracts were concentrated under vacuum to give 70-75 L of a yellow methyl isobutyl ketone solution of (S)-3-bromo-5-(1-methylpyrrolidin-2-yl)pyridine (II).

Sodium Iodide (12.10 kg, 79.93 mol, 2.0 equiv), cuprous iodide (0.38 kg, 2.00 mol, 0.050 equiv.) and N,N'-dimethylethylenediamine (0.35 kg, 4.00 mol, 0.10 equiv.) were added to the solution. The solution was heated to 105° C. and held 12 hours. UPLC/MS analysis confirmed conversion to the iodide was complete and the reaction cooled to 20° C.

Methyl isobutyl ketone (23.4 L), water (28 L) and ammonium hydroxide (28 mass %, 28 L) were added. The phases were split after stirring 30 min. The lower dark blue aqueous phase was discarded. The upper amber organic phase containing product was washed with water (46.8 L) and concentrated under vacuum to ~12 L.

(S)-3-iodo-5-(1-methylpyrrolidin-2-yl)pyridine (IV) (9.66 kg, 33.43 mol, 86.3%, corrected yield) was isolated as an amber methyl isobutyl ketone solution.

$^1$H NMR (400 MHz, DMSO-d$_6$) δ 1.58 (m, 1H), 1.75 (m, 1H), 1.85 (m, 1H), 2.08 (s, 3H), 2.18 (m, 1H), 2.25 (q, 1H), 3.10 (t, 1H), 3.15 (td, 1H), 8.09 (t, 1H), 8.50 (d, 1H), 8.69 (d, 1H).

$^{13}$C NMR (400 MHz, DMSO-d$_6$) δ 22.3, 34.9, 40.0, 56.3, 67.1, 94.4, 141.5, 142.6, 147.6, 153.8.

HRMS: (ESI+) Calcd for C$_{10}$H$_{14}$N$_2$I (M+H)+: 289.01962. Found: 289.02002 (dev. 1.0 ppm).

Preparation 5: (S)-2-(5-(1-methylpyrrolidin-2-yl)pyridin-3-yloxy) ethanol (V)

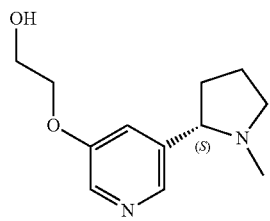

Potassium carbonate (10.74 kg, 77.74 mol, 2.00 equiv.) and cuprous iodide (0.74 kg, 3.89 mol, 0.10 equiv.) were added to a solution of (S)-3-iodo-5-(1-methylpyrrolidin-2-yl)pyridine (IV) (11.20 kg, 38.87 mol, 1.00 equiv.) in anhydrous ethylene glycol (46 L). The viscous reaction mixture was heated to 100° C., giving an easily stirred dark red solution.

UPLC/MS analysis after 4 h at 100° C. indicated the reaction was complete. The product was extracted from ethylene glycol with seven extractions of a mixture of toluene (31.36 L) and dichloromethane (31.36 L). All extracts were combined and the solution concentrated under vacuum (~90 L).

Potassium carbonate (10.74 kg, 77.74 mol, 2.00 equivalents) was charged to the toluene solution and the mixture stirred 18 hours at 20° C. The mixture was filtered through a diatomaceous earth coated filter. The green solids were washed twice with toluene (22.4 L) and the combined filtrates concentrated under vacuum (~25 L). (S)-2-(5-(1-methylpyrrolidin-2-yl)pyridin-3-yloxy) ethanol (V) (6.99 kg, 31.37 mol, 80.9%, corrected yield) was isolated as a toluene solution.

$^1$H NMR (400 MHz, DMSO-d$_6$) δ 1.60 (m, 1H), 1.76 (m, 1H), 1.85 (m, 1H), 2.08 (s, 3H), 2.16 (m, 1H), 2.24 (q, 1H), 3.11 (t, 1H), 3.15 (td, 1H), 3.72 (b, 2H), 4.06 (m, 2H), 4.91 (b, 1H), 7.28 (dd, 1H), 8.11 (b, 1H), 8.18 (b, 1H).

$^{13}$C NMR (400 MHz, DMSO-d$_6$) δ 22.2, 34.9, 40.0, 56.3, 59.4, 67.7, 69.8, 119.2, 136.6, 139.8, 141.0, 155.1.

HRMS: (ESI$^+$) Calcd for C$_{12}$H$_{19}$N$_2$O$_2$ (M+H)$^+$: 223.14410, Found: 223.04420 (dev. 0.4 ppm).

Preparation 6: (S)-2-(5-(1-methylpyrrolidin-2-yl)pyridin-3-yloxy)ethyl 4-methylbenzenesulfonate (VI)

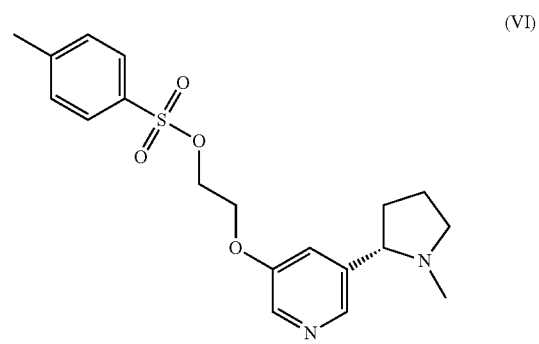 [SMILES: Cc1ccc(S(=O)(=O)OCCOc2cncc([C@@H]3CCCN3C)c2)cc1]

A toluene solution of (S)-2-(5-(1-methylpyrrolidin-2-yl)pyridin-3-yloxy)ethanol (V) (33 L/7.00 kg, 31.49 mol, 1 equiv) was added over 15 minutes to a dichloromethane (56 L) solution of p-toluenesulfonyl chloride (9.01 kg, 47.24 mol, 1.5 equiv.) and N-methylimidazole (5.17 kg, 62.98 mol, 2.0 equiv.) at −10° C. The yellow suspension was held 1 hour at −10° C. then warmed to 10° C. over 30 minutes and held an additional hour. UPLC analysis determined the reaction was complete.

The reaction was quenched with a solution of potassium carbonate (15.23 kg, 110.22 mol, 3.50 equivalents) in water (55 L) and warmed to 20° C. The phases were split and the organic layer was washed with a solution of sodium chloride (10.12 kg) in water (56 L). Both aqueous layers were discarded.

The product was extracted into a solution of citric acid (12.10 kg, 62.98 mol, 2.0 equivalents) in water (28 L) and the toluene/dichloromethane layer was also discarded. Tert-butyl methyl ether (140 L) was added followed by an aqueous solution of potassium hydroxide (45 wt %, 24.34 kg, 6.2 equiv.). The phases were split and the organic layer washed with a solution of sodium chloride (10.12 kg) in water (56 L). The tert-butyl methyl ether solution was stirred with Darco® KB-B (0.70 kg, 10 wt %) at 35° C. for 1 hour before filtering through a bed of sodium sulfate. The solids were washed three times with tert-butyl methyl ether (7.0 L). All filtrates were combined and transferred through a 0.5 micron filter to remove carbon particulates. The solution was concentrated (~70 L) under vacuum at 30° C., then cooled to 15° C. Crystallization began spontaneously with cooling. The suspension was stirred 1 hour at 15° C. then heptane (70 L) was added. The mixture was cooled to 0° C. and stirred an additional hour.

The white solids filtered from the mixture were washed twice with heptane (35 L) and dried on the filter giving (S)-2-(5-(1-methylpyrrolidin-2-yl)pyridin-3-yloxy)ethyl 4-methylbenzenesulfonate (VI) (7.97 kg, 21.17 mol, 67% corrected yield).

$^1$H NMR (400 MHz, DMSO-d$_6$) δ 1.57 (m, 1H), 1.76 (m, 1H), 1.84 (m, 1H), 2.07 (s, 3H), 2.14 (m, 1H), 2.24 (q, 1H), 2.42 (s, 3H), 3.09 (t, 1H), 3.15 (td, 1H), 4.24 (m, 2H), 4.36 (dd, 2H), 7.17 (dd, 1H), 7.47 (d, 2H), 7.80 (d, 2H), 8.05 (s, 1H), 8.10 (s, 1H).

$^{13}$C NMR (400 MHz, DMSO-d$_6$) δ 21.1, 22.2, 34.9, 40.0, 56.3, 65.6, 67.6, 69.0, 119.3, 127.7, 130.1, 132.2, 136.4, 139.8, 141.5, 145.0, 154.1.

HRMS: (ESI+) Calcd for $C_{19}H_{25}N_2O_4S$ (M+H)+: 377.152895. Found: 377.15268 (dev. −0.7 ppm).

Preparation 7: (S)-2-(5-(1-methylpyrrolidin-2-yl)pyridin-3-yloxy)ethanamine 4-methylbenzenesulfonate (VII)

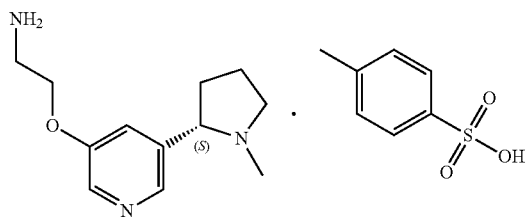

(VII)

(S)-2-(5-(1-methylpyrrolidin-2-yl)pyridin-3-yloxy) ethyl-4-methylbenzenesulfonate (VI) (7.92 kg, 21.04 mol) was dissolved in 7N ammonia in methanol (95 L) in a pressure reactor. The solution was heated to 65-75° C. to maintain reaction pressure at 45-50 psi.

After eight hours, the reaction was cooled to 20° C. UPLC analysis determined the reaction was complete.

The reaction solution was diluted with methanol (80 L), and then concentrated under vacuum (maximum 40° C.) to remove ammonia. Additional methanol was added during concentration to maintain a constant volume of 75-80 L. Concentration was continued until the pH of the solution remained steady at 7.5, ensuring all ammonia was removed.

The methanol concentrate was transferred to a spec and fiber free vessel through a 0.5 um cartridge filter. Acetonitrile (118.8 L) was added and the solution concentrated under vacuum (45-50° C.) to remove methanol. Additional acetonitrile was added during concentration to maintain a constant volume of 75-80 L. Concentration was continued until crystallization was apparent. The mixture was cooled and the suspension granulated at 5° C. for eighteen hours.

The white solids filtered from the mixture were washed with acetonitrile and vacuum dried at 50° C. for twelve hours giving (S)-2-(5-(1-methylpyrrolidin-2-yl)pyridin-3-yloxy)ethanamine-4-methylbenzenesulfonate (VII) (6.0 kg, 15.27 mol, 72.5% corrected yield).

$^1$H NMR (600 MHz, DMSO-$d_6$) δ 1.60 (m, 1H), 1.78 (m, 1H), 1.85 (m, 1H), 2.10 (s, 3H), 2.08 (m, 1H), 2.27 (m, 1H), 2.29 (s, 3H), 3.15 (m, 1H), 3.17 (m, 1H), 3.24 (m, 2H), 4.24 (m, 2H), 7.11 (d, 1H), 7.32 (dd, 1H), 7.48 (d, 2H), 7.91 (b, 2H), 8.16 (d, 1H), 8.22 (d, 1H).

$^{13}$C NMR (600 MHz, DMSO-$d_6$) δ 20.8, 22.2, 34.9, 38.4, 40.0, 56.3, 64.8, 67.5, 119.6, 125.5, 128.1, 136.7, 137.7, 139.8, 141.8, 145.6, 154.3.

HRMS: (ESI+) Calcd for $C_{12}H_{20}N_3O$ (M+H)+: 222.15971. Found: 222.16009 (dev.-1.7 ppm)(free base); (ESI$^+$) Calcd for $C_{19}H_{27}N_3SO_4$ (M+H)$^+$: 394.17950, Found: 394.17873 (mono salt).

Preparation 8: (S)-2-((5-(1-methylpyrrolidin-2-yl)pyridin-3-yl)oxy)ethan-1-amine bis(4-methylbenzenesulfonate) dihydrate (VIII)

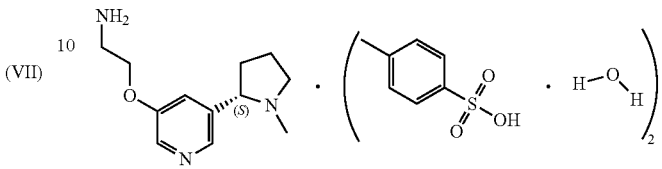

(VIII)

(S)-2-(5-(1-methylpyrrolidin-2-yl)pyridin-3-yloxy)ethanamine-4-methylbenzenesulfonate (VII) (5.00 g, 12.7 mmol) and P-toluenesulfonic acid (98 mass %, 2.42 g, 12.7 mmol) were dissolved together in methanol (25 ml). The solution was concentrated under vacuum (45-50° C.) to remove methanol. Acetonitrile was added during concentration to maintain a constant volume of 100 ml. Concentration was continued until two liquid phases were apparent. The mixture was cooled to 22° C., and water (2.29 ml, 127 mmol) was added slowly to the stirred mixture. Crystallization was evident with the water addition and the suspension was granulated 30 minutes.

The white solids filtered from the mixture were washed twice with acetonitrile and vacuum dried at 50° C. for eighteen hours giving S)-2-((5-(1-methylpyrrolidin-2-yl)pyridin-3-yl)oxy)ethan-1-amine bis(4-methylbenzenesulfonate) dihydrate (VIII) (5.96 g, 10.54 mmol, 83% yield).

$^1$H NMR (DMSO-$d_6$, 600 MHz, 25° C.): δ 9.82 (b, 1H), 8.41 (d, J=2.7 Hz, 1H), 8.35 (d, J=1.5 Hz, 1H), 8.02 (b, 3H), 7.66 (b, 1H), 7.50 (d, J=8.1 Hz, 4H), 7.13 (d, J=8.1 Hz, 4H), 4.47 (b, 1H), 4.34-4.24 (m, 2H), 3.76 (b, 1H), 3.30-3.19 (b, 3H), 2.69 (b, 3H), 2.47-2.40 (m, 1H), 2.29 (s, 6H), 2.25-2.06 (m, 3H).

$^{13}$C NMR (DMSO-$d_6$, 150.8 MHz, 25° C.): δ 154.2, 145.2 (2X), 142.6, 139.7, 138.0 (2X), 129.7, 128.2 (2X), 125.5 (2X), 120.6, 68.6, 64.9, 55.4, 38.3, 37.9, 30.6, 21.2, 20.8 (2X).

HRMS: (ESI$^+$) Calcd for $C_{12}H_{20}N_3O$ (M+H)$^+$: 222.16009, Found: 222.15948 (free base).

Note: Both amino and methyl-pyrrolidine groups are protonated. The molar ratio of free base to p-toluenesulfonic acid is 1:2.

Also within the scope of the invention are intermediate compounds as hereinbefore defined, all salts, solvates and complexes thereof and all solvates and complexes of salts thereof as defined hereinbefore for the compounds. The invention includes all polymorphs of the aforementioned species and crystal habits thereof.

When preparing compounds in accordance with the invention, it is open to a person skilled in the art to routinely select the form of compound which provides the best combination of features for this purpose. Such features include the melting point, solubility, processability and yield of the intermediate form and the resulting ease with which the product may be purified on isolation.

The invention claimed is:
1. A compound of formula (IIIA):
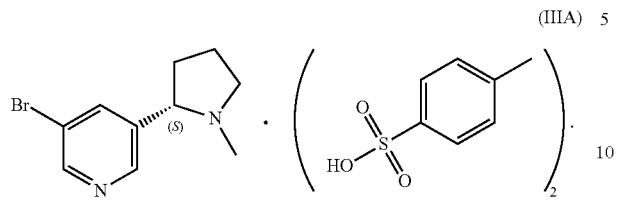
* * * * *